(12) United States Patent
Taguchi (10) Patent No.: US 11,052,171 B2
(45) Date of Patent: *Jul. 6, 2021

(54) METHOD OF HEMOSTASIS (71) Applicant: NATIONAL INSTITUTE FOR MATERIALS SCIENCE, Tsukuba (JP)

(72) Inventor: Tetsushi Taguchi, Tsukuba (JP)

(73) Assignee: NATIONAL INSTITUE FOR MATERIALS SCIENCE, Tsukuba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/396,561

(22) Filed: Apr. 26, 2019

(65) Prior Publication Data
US 2019/0247537 A1 Aug. 15, 2019

Related U.S. Application Data

(63) Continuation of application No. PCT/JP2017/038325, filed on Oct. 24, 2017.

(30) Foreign Application Priority Data

Oct. 26, 2016 (JP) .............................. JP2016-209262

(51) Int. Cl.
*A61L 24/10* (2006.01)
*A61L 24/00* (2006.01)
(Continued)

(52) U.S. Cl.
CPC ............. *A61L 24/104* (2013.01); *A61L 15/32* (2013.01); *A61L 24/0005* (2013.01); *A61L 24/10* (2013.01); *A61L 31/04* (2013.01)

(58) Field of Classification Search
None
See application file for complete search history.

(56) References Cited

U.S. PATENT DOCUMENTS 8,314,211 B2* 11/2012 Falus .................... A61L 24/043
530/381
10,668,181 B2* 6/2020 Taguchi .............. A61L 24/0005
(Continued)

FOREIGN PATENT DOCUMENTS

JP 09-103479 A 4/1997
JP 2010521994 A 7/2010
(Continued)

OTHER PUBLICATIONS

Matsuda (Matsuda, S., et al., Bioadhesion of gelatin films crosslinked with glutaraldehyde, J. Biomed. Mater. Res, 45 (1999) pp. 20-27). (Year: 1999).*
(Continued)

*Primary Examiner* — Dominic Lazaro
(74) *Attorney, Agent, or Firm* — Liang Legal Group, PLLC (57) ABSTRACT

A method of hemostasis includes the step of applying a hemostatic agent to an affected site of a subject, the hemostatic agent consisting of a first agent comprising a gelatin derivative having a hydrophobic group bonded to the gelatin via an imino group, wherein the gelatin derivative has (a) a weight average molecular weight of from 10,000 to 50,000, (b) the hydrophobic group, which is an alkyl group having 6 to 18 carbon atoms; and (c) a molar ratio of imino group/amino group of the gelatin derivative ranging from 1/99 to 30/70; and a second agent including a crosslinking agent for the gelatin derivative.

6 Claims, 5 Drawing Sheets

(51) Int. Cl.
*A61L 15/32* (2006.01)
*A61L 31/04* (2006.01)

(56) References Cited

U.S. PATENT DOCUMENTS

2002/0155398 A1* 10/2002 Yanagi ................ G03C 1/0051
    430/567
2013/0220174 A1    8/2013 Taguchi et al.
2015/0359924 A1* 12/2015 Taguchi ................ A61L 24/104
    106/150.2

FOREIGN PATENT DOCUMENTS

| | | |
|---|---|---|
| JP | 2012095769 A | 5/2012 |
| JP | 5995128 B1 | 9/2016 |
| JP | 2017127497 A | 7/2017 |
| WO | 2012046717 A1 | 4/2012 |
| WO | 2014112208 A1 | 7/2014 |

OTHER PUBLICATIONS

Sarika (Sarika, P. R., et al., Modified gum arabic cross-linked gelatin scaffold for biomedical applications, Mater. Sci. Eng. C. Mater. Biol. Appl., 43 (2014) pp. 272-279). (Year: 2014).*

Taguchi, Tetsushi, Development trend of medical adhesive with high biocompatibility, (Japanese) Engineering Materials, Jun. 2015, vol. 63, No. 6, pp. 44-50.

* cited by examiner

METHOD OF HEMOSTASIS

CROSS-REFERENCE TO RELATED APPLICATIONS

This is a Continuation of International Application No. PCT/JP2017/038325, filed on Oct. 24, 2017, which claims priority of Japanese application No. 2016-209262, filed on Oct. 26, 2016. The disclosures of these prior applications are incorporated by reference in their entirety.

TECHNICAL FIELD

The present invention relates to a method of hemostasis comprising the step of applying a hemostatic agent to an affected site of a subject, which hemostatic agent comprises a gelatin derivative having a hydrophobic group bonded thereto.

BACKGROUND ART

Hemostasis by applying a hemostatic agent to tissues of an affected site of a subject such as a surgical incision or a skin wound is widely practiced in various surgical operations such as those in thoracic surgery, gastrointestinal surgery, cardiovascular surgery, oral and maxillofacial surgery and so on. The hemostatic agents currently used include collagen-based hemostatic agents, gelatin-based hemostatic agents, and fibrin-based hemostatic agents.

An example of the collagen-based hemostatic agent is a sheet made by crosslinking cotton-like fibers spun from calf dermis-derived atelocollagen with a polyepoxy compound (Integran (trade name), Koken Co. Ltd). An example of the gelatin-based hemostatic agent is a combination of crosslinked gelatin particles and human thrombin (Floseal (trade name), Baxter Ltd). A problem with these hemostatic agents lies in complexity of manufacturing processes such as crosslinking process, and sheet- or particle-molding process. In addition, human thrombin is obtained from blood preparation which inherently has a risk of virus infection.

Another example of the hemostatic agent comprises a gelatin-resorcinol mixed solution and a formalin solution, which are mixed and then applied to a bleeding site where a crosslinking occurs. Formalin, however, has histotoxic problem of crosslinking proteins in vivo.

The fibrin-based hemostatic agent is based on the second stage of hemostasis in vivo where fibrinogen is converted to fibrin polymer which forms a meshwork around platelet plugs formed in the first stage of the hemostasis to stop breeding. Fibrin adheres to the tissue of organs such as the blood vessel, so that it brings about hemostasis through sealing an anastomotic part and a damaged site (hereinafter referred to as "sealing effect.") This sealing effect is sometimes regarded as "hemostatic effect", but it is different from the effect of blood coagulation. For example, the sealant (BioGlue (trade name), Cryo Life, Inc.), where bovine serum albumin is crosslinked with glutaraldehyde, has the sealing effect, but does not coagulate blood, so that it does not fall under the category of hemostatic agent in the present invention. On the other hand, the aforesaid collagen-based hemostatic agent has the effect of blood coagulation but lacks the sealing effect. In contrast, the fibrin-based hemostatic agent has both sealing and blood coagulation effects, so that it has been intensively studied for clinical application. Examples of the fibrin-based hemostatic agent include Tisseel VH (trade name, Baxter Ltd.), and Evicel (trade name, Johnson & Johnson K.K.).

The fibrin-based hemostatic agent, however, has a risk of virus infection because it is produced from a blood product. Further, Ca ion is inevitable to convert fibrinogen to fibrin polymer, so that the use of a blood product comprising an anticoagulant such as sodium citrate has a difficulty in blood coagulation although calcium chloride solution is provided with the hemostatic agent in addition to Factor XIII etc.

Meanwhile, the inventor has been developing surgical sealants comprising a gelatin derivative having a hydrophobic group bonded to the gelatin (hereinafter, may be referred to as "hydrophobically modified gelatin") The surgical sealants have an excellent adhesive property to the tissue of a subject and, after applied to the tissue, they are degraded in vivo (Patent literatures 1, 2).

CITATION LIST

Patent Literature

Patent Literature 1: WO2012/046717
Patent Literature 2: WO2014/112208

SUMMARY OF INVENTION

Technical Problem

The inventor has found, while improving a surgical sealant in manufacturing process and sterilization resistance (JP 5995128, co-pending U.S. Ser. No. 16/071,625), that the surgical sealant has an excellent hemostatic property to solve the aforesaid problems of the currently used hemostatic agents.

Solution to Problem

The present invention provides a method of hemostasis, comprising the step of applying a hemostatic agent to an affected site of a subject, the hemostatic agent consisting of a first agent comprising a gelatin derivative having a hydrophobic group bonded to the gelatin via an imino group, wherein the gelatin derivative has
 (a) a weight average molecular weight of from 10,000 to 50,000,
 (b) the hydrophobic group, which is an alkyl group having 6 to 18 carbon atoms; and
 (c) a molar ratio of imino group/amino group of the gelatin derivative ranging from 1/99 to 30/70; and
a second agent comprising a crosslinking agent for the gelatin derivative.

Advantageous Effects of Invention

As mentioned above in Background Art, a hemostatic agent comprising gelatin has been used. A hemostatic agent comprising a hydrophobically modified gelatin, however, has not yet been known. The hydrophobically modified gelatin shows comparable or superior blood coagulation effect to the non-modified gelatin. In addition, it has a superior adhesion property to the tissue of a subject, so that it can be advantageously used for hemostasis at the affected sites where a hemostatic agent is difficult to fix such as the upper gingiva, and the palate. The blood coagulation effect of the hemostatic agent is produced without Ca ion, so that the hydrophobically modified gelatin-based hemostatic agent is useful when a blood product for transfusion comprising an anticoagulant is used. Further, as mentioned above, the hemostatic agent of the present invention exerts an excellent sealing effect and, compared with a fibrin-based hemostatic agent, is superior both in the sealing and hemostatic effects as well as no risk of virus infection. The hemostatic agent of the present invention is very useful in various surgical operations.

DETAILED DESCRIPTION

The First Agent

Figure 1:
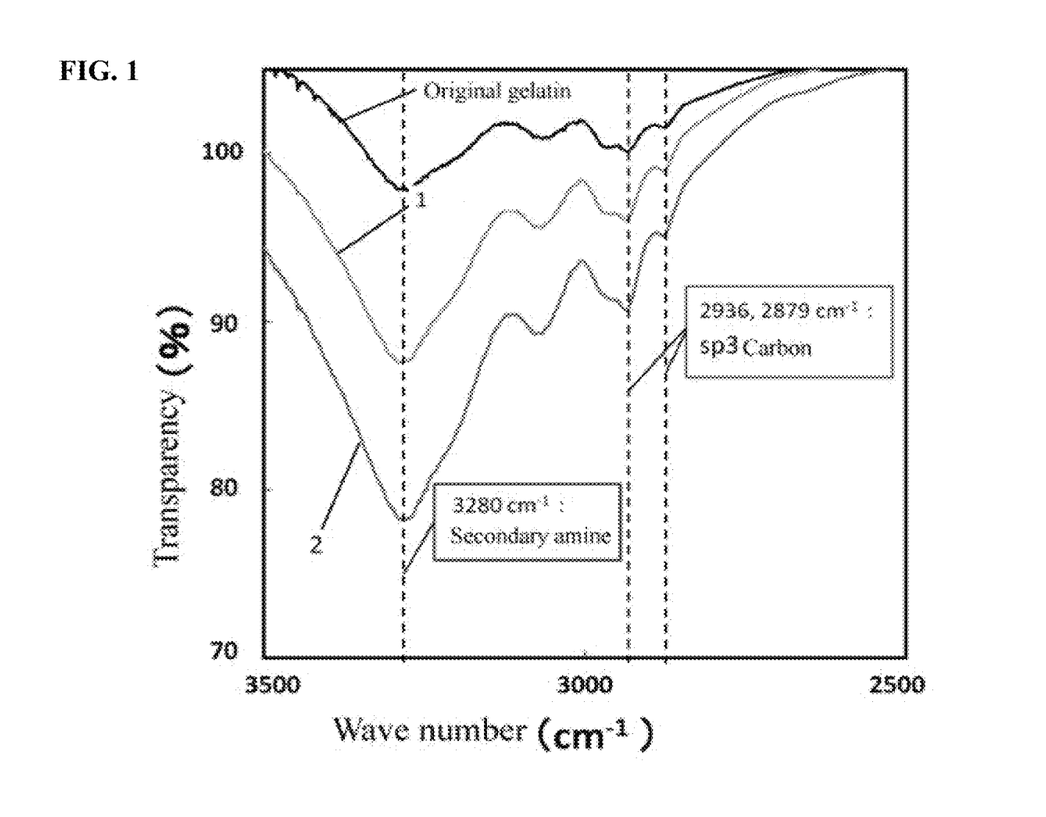
FIG. 1 shows FT-IR spectra of an original gelatin and gelatin derivatives.

In the present invention, the first agent of the hemostatic agent comprises a gelatin derivative. The gelatin derivative has a hydrophobic group bonded via an imino group, preferably —NH—, to have the structure represented by the following formula:

$$GltnNH\text{—}CHR^1R^2 \quad (1)$$

wherein "Gltn" represents a gelatin residue, $R^1$ is the hydrophobic group, and $R^2$ is a hydrogen atom or the hydrophobic group. In the above structure, "N" mainly originates from ε-amino group of lysine (Lys) in the gelatin. Preferably, $R^2$ is a hydrogen atom. The NH structure in the formula (1) can be identified by, for example, an absorption band around 3300 cm$^{-1}$ in FT-IR spectrum. FIG. 1 shows FT-IR spectra of the gelatin derivatives (Alaska-pollock derived gelatin having a molecular weight (Mw) of 13,000 derivatized with dodecyl group at a derivatization ratio of 4.2 mol % (spectrum 1) and 8.9 mol % (spectrum 2)) with a spectrum of the original gelatin for comparison. It can be seen that N—H vibration around 3300 cm$^{-1}$ and C—H vibration around 2900 cm$^{-1}$ become stronger with an increased amount of hydrophobic group.

When $R^2$ is the hydrophobic group, it may be the same as or different from $R^1$. The hydrophobic group is an alkyl group having 6 to 18 carbon atoms, which may be branched. Examples of the alkyl group include hexyl group, octyl group (or caprylic group), nonyl group (or pelargonyl group), decyl group, dodecyl group (or lauryl group), and tetradecyl croup (or myristyl group). Preferably, $R^1$ is a linear alkyl group having 6 to 15 carbon atoms, more preferably from 7 to 13, most preferably from 7 to 11 and $R^2$ is a hydrogen atom.

A ratio of derivatization in the gelatin derivative is defined as a mol % of the imino group to which the hydrophobic group is bonded relative to an amount of the amino group in the original gelatin, and ranges from 1 to 30 mol %, preferably from 1 to 20 mol %, more preferably from 5 to 10 mol %. In other words, a molar ratio, imino group/amino group, in the obtained gelatin derivative ranges from 1/99 to 30/70, preferably from 1/99 to 20/80, more preferably from 5/95 to 10/90. The ratio of derivatization can be determined by quantifying the amino group of the original gelatin and that of the gelatin derivative through titration by using 2,4,6-trinitrobenzen sulfonic acid method, or by a quantitative identification of the hydrophobic group with NMR.

The gelatin derivative has a weight average molecular weight (Mw) of from 10,000 to 50,000, preferably from 10,000 to 40,000, more preferably from 20,000 to 35,000. In the range, an excellent resistance to electron beam sterilization is observed. The molecular weight can be determined by gel permeation chromatography (GPC) according to a conventional procedure.

The original gelatin may be of natural origin, chemically synthesized, fermented, or genetically modified gelatin. Preferably, a gelatin of natural origin is used such as the one derived from bovine, porcine, or fish gelatin, more preferably cold-water fish gelatin such as sea bream or codfish gelatin, and most preferably codfish gelatin, particularly Alaska pollock gelatin. The cold-water fish gelatin contains less imino acid than the porcine gelatin, so that it can make a sealant having a good fluidity at room temperature even at a high concentration thereof.

The original gelatin may be an acid-treated gelatin or an alkaline-treated gelatin. Preferably, it is an alkaline-treated gelatin. A molecular weight thereof may be in such a range that the gelatin derivative has the aforesaid average molecular weight (Mw).

The first agent may comprise non-derivatized gelatin in addition to the gelatin derivative. As the gelatin, the aforesaid various kinds of gelatin may be used. The non-derivatized gelatin may be contained in an amount of from 0 to 99 wt %, preferably 0 to 50 wt % of a total weight of the derivatized and the non-derivatized gelatin.

The first agent may further comprise an aqueous solvent, and from the convenience viewpoint, it is provided preferably in the form of an aqueous liquid by dissolving or dispersing the gelatin derivative in the aqueous solvent, hereinafter may be simply referred to as "aqueous solution." The aqueous solvent may be ultrapure water, saline, buffer solution containing acid such as boric acid, phosphoric acid, or carbonic acid and a salt thereof, or a mixture of these solvents. Preferably, a borate buffer having a pH of from 8 to 11, more preferably from 9 to 10, most preferably from 9.3 to 9.7 is used. The aqueous solvent is used in such an amount that a concentration of the gelatin derivative ranges from 10 to 80 wt/v %, preferably from 15 to 30 wt/v %. Such an aqueous solution has an ionic strength of from 0.01 to 0.5 mol/L, preferably from 0.05 to 0.2 mol/L. When the non-derivatized gelatin is contained, a total concentration of the gelatin derivative and non-derivatized gelatin falls in the aforesaid concentration.

Second Agent

In the present invention, the second agent is a crosslinking agent for the gelatin derivative, which forms a structure insoluble in water or body fluids such as blood. At least one kind of the crosslinking agent is used, which crosslinking agent has at least two functional groups per molecule reactive with the amino groups in gelatin, mainly the primary amino group at side chains. Examples of the crosslinking agent include genipin, polybasic acids activated with N-hydroxysuccinimide or N-hydroxysulfosuccinimide, aldehyde compounds, acid anhydrides, dithiocarbonate and diisothiocyanates.

Examples of the polybasic acid include tartaric acid, citric acid, malic acid, glutaric acid, glutamic acid, aspartic acid, oxaloacetic acid, cis-aconitic acid, 2-ketoglutaric acid, polytartaric acid, polycitric acid, polymalic acid, polyglutamic acid, polyaspartic acid, and active-esterified derivatives thereof such as disuccinimidyl glutarate (DSG), disuccinimidyl suberate (DSS), and disuccinimidyl tartrate (DST).

Other examples of the polybasic acid include polybasic acid esters of polyethylene glycol or polyethylene glycol ethers with at least one carboxyl group, which remained unreacted with polyethylene glycol, being active-esterified such as 4,7,10,13,16-penta-oxanonadecanoic acid di (N-succinimidyl), and polyethylene glycol di(succinimidyl succinate) (SS-PEG-SS) represented by the following formula:

wherein n is such a number that Mn is about 20,000; and pentaerythritol polyethylene glycol ether tetrasuccinimidyl glutarate (4S-PEG) represented by the following formula:

wherein n is such a number that Mw ranges from about 3,000 to 30,000, preferably from about 5,000 to 27,000, more preferably from about 15,000 to 25,000.

Examples of the aldehyde compounds include polysaccharides to which at least two aldehyde groups are introduced such as aldehyde group-introduced starch, aldehyde group-introduced dextran, and aldehyde group-introduced hyaluronic acid. Examples of the acid anhydride include glutaric acid anhydride, maleic acid anhydride, and succinic acid anhydride. An example of diisothiocyanate is hexamethylene diisothiocyanate. Among these, aforesaid activated polybasic acid ester of polyethylene glycol, and aldehyde group-introduced polysaccharides are preferably used.

The crosslinking agent is used in such an amount that a functional group, for example, an ester group activated with N-hydroxysuccinimide, in the crosslinking agent per mole of the amino group of the gelatin derivative ranges from 0.1 to 3 equivalents, preferably from 0.2 to 2 equivalents, more preferably from 0.3 to 1.5 equivalents, and most preferably from 0.3 to 0.8 equivalent. A mixture of two or more kinds of the crosslinking agents may be used in such an amount that a total equivalent amount thereof falls in the above range.

The second agent, too, preferably comprises an aqueous solvent to dissolve the crosslinking agent. It should be noted that preferably the crosslinking agent and the aqueous solvent are provided in separate containers, and at most about 2 hours before the use adequate amounts thereof are mixed into an aqueous solution, which may be hereinafter referred to as "aqueous solution." As the aqueous solvent, the aqueous solvents mentioned above for the first agent can be used. Preferably, a phosphate buffer having a pH of from 3 to 8, more preferably from 4 to 6, is used. Most preferably, ionic strengths of the aqueous solvent for the first agent and that for the second agent are adjusted so that a mixture of the same volume of the first agent solution and the second agent solution has a pH of from about 8 to about 10. For example, an aqueous solution of the first agent in a borate buffer having a pH of 9 and an ionic strength of 0.05 to 0.1, and an aqueous solution of the second agent in a phosphate buffer having a pH of 4 and an ionic strength of from 0.01 to 0.03 can make an equivolume mixed solution having a pH of the aforesaid range. Another example is a combination of an aqueous solution of the first agent in a borate buffer having pH 10 and an ionic strength of 0.05 to 0.1, and an aqueous solution of the second agent in a phosphate buffer having a pH of 4 and an ionic strength of from 0.01 to 0.07.

A concentration of the second agent is adjusted so that an equivalent amount of a functional group of the second agent relative to an equivalent amount of the amino group in the first agent, i.e., (an equivalent amount of a functional group of the second agent/an equivalent amount of the amino group in the first agent), falls in the range mentioned above. A mixture of two or more kinds of the crosslinking agents may be used in such an amount that a total amount thereof falls in the aforesaid range.

Additives

The aforesaid first agent and/or the second agent may comprise various additives in such an amount that they do not adversely affect the object of the present invention. Examples of the additives include colorants, pH adjusting agents, viscosity modifiers, and preservatives or the like. Preferably, in order to highlight the applied site of the hemostatic agent, an aqueous solution of the first agent or the second agent comprises a colorant such as blue colorant, for example, brilliant blue, in an amount of from 10 to 100 μg/mL.

Manufacturing Method

The hemostatic agent in the present invention can be produced by preparing the first agent and the second agent separately.

Preparation of the First Agent (1) Preparation of an Aqueous Solution of an Original Gelatin A starting material, i.e., original gelatin, is dissolved in an aqueous solvent at a concentration of from 5 to 50 wt/v % by heating at 40 to 90° C. The aqueous solvent may be a mixture of water and a water-soluble organic solvent. Examples of the organic solvent include alcohols having 1 to 3 carbon atoms and esters having 1 to 3 carbon atoms, among which ethanol is preferably used.

(2) Derivatization

To the aqueous solution of the gelatin obtained in the step (1), a derivatizing agent having a hydrophobic group to be introduced to the gelatin is added and a mixture thus obtained is subjected to a reaction for a predetermined period of time while stirring. As the derivatizing agent, an aldehyde or a ketone having the hydrophobic group is used such as dodecanal, tetradecanal, and decyl ethyl ketone. A reaction temperature ranges from 30 to 80° C., and a reaction time ranges from 0.5 to 12 hours. A gelatin derivative having an alkyl group bonded to an amino group of the gelatin in the form of a Schiff base (GltnN=$CR^1R^2$) can usually be obtained merely by stirring. The aldehyde is used in an amount of from 1 to 4 times, more preferably from 1 to 2 times, the stoichiometric amount corresponding to a desired derivatization ratio.

Subsequently, the Schiff base is reduced to the structure of the above formula (1). A known reducing agent can be used such as sodium cyanoborohydride ($NaBH_3CN$), sodium triacetoxyborohydride ($NaBH(OAc)_3$), 2-picoline borane, and pyridine borane, among which 2-picoline borane is preferred because it is stable to allow a one-pot reductive amination reaction of aldehydes or ketones in an aqueous solvent. In addition, a yield of from 80 to 90% can be achieved, which is significantly higher than 70 to 75% achieved by sodium cyanoborohydride. Preferably, 2-picoline borane is used in an amount of from 1 to 3 equivalents relative to an equivalent of a derivatizing agent.

(3) Purification

The reaction mixture solution from the step (2) is added to an excess amount of a poor solvent such as cold ethanol to precipitate a gelatin derivative. After isolating the precipitate by filtration, it is washed with ethanol or the like to obtain a final product.

(4) Preparation of the First Agent

The gelatin derivative obtained in the step (3) is preferably dissolved in an aqueous solvent such as borate buffer in such an amount mentioned above. The non-derivatized gelatin or the additives may be incorporated as desired. The first agent obtained is packed in a container, for example, plastic dispenser. Preferably, the aqueous solution of the first agent is placed in one of the syringes of a dual syringe dispenser used for applying the hemostatic agent to an affected part, which dispenser can mix two agents at a tip thereof.

Preparation of the Second Agent

The above crosslinking agents as mentioned above may be synthesized with known methods or purchased. The crosslinking agent and an aqueous solvent to dissolve the agent such as a phosphate buffer are provided in separate containers, for example, the crosslinking agent in a glass vial and the aqueous solvent in a plastic bottle, and the crosslinking agent is dissolved in the aqueous solvent at most about 2 hours before the use.

Radiation Sterilization

Subsequently, the first agent in the form of an aqueous solution placed in a dispenser, and the second agent in the form of a combination of the crosslinking agent powder packed in a vial and an aqueous solvent to dissolve the crosslinking agent in a bottle may be radiation sterilized. Alternatively, the gelatin derivative powders packed in a vial and an aqueous solvent in a bottle (solvent for the first agent), and the crosslinking agent powders packed in a vial and an aqueous solvent to dissolve the crosslinking agent in a bottle (solvent for the second agent) are each radiation sterilized. The radiation may be electron beam radiation, gamma ray radiation, or bremsstrahlung radiation, among which electron beam sterilization is preferred. A total absorbed dose may be at least 25 kGy, which is widely employed (Japanese Pharmacopoeia, Fourteenth Edition, Part Two, Reference Information, page 1235, right column, 2.2 Radiation Method), preferably ranges from 25 kGy to 45 kGy. The hemostatic agent may be provided in the form of kit comprising the sterilized first agent, the second agent, the aqueous solvents and an instruction manual, or provided in a combination and amounts as required by the user.

Method of Application to an Affected Site of a Subject

The method of hemostasis of the present invention can be used for various surgical incisions, skin wounds or the like, for example, in thoracic surgeries such as lung adenocarcinoma, squamous cell carcinoma, large cell cancer, small cell cancer, and emphysema surgeries; gastrointestinal surgeries such as liver cancer, stomach cancer, esophagus cancer, and pancreatic cancer surgeries; oral and maxillofacial surgeries such as enamel epithelial tumor, odontoma, jawbone osteomyelitis, bisphosphonate related jaw bone necrosis, root cyst, dentate cyst, odontogenic keratocyst, postoperative maxillary cyst, mucous cyst, epidermoid cyst surgeries; cardiovascular surgeries such as dissecting aortic aneurysm, heart valve disease, atrial septal defect, thoracic aortic aneurysm, meningioma, hearing nerve tumor, pituitary adenoma, craniopharyngioma, glioma, central nervous system primary malignant lymphoma, medulloblastoma, cranial germ cell tumor, metastatic brain tumor surgeries; and other kinds of cancer surgeries such as prostate cancer, bladder cancer, renal pelvic cancer, penile cancer, retroperitoneal cancer, adrenal cancer, head and neck cancer, thyroid cancer, uterine cancer, cervical cancer, ovarian cancer, and bone metastasis surgeries. In particular, the hemostasis method is effectively used in various cancer surgeries such as liver cancer, stomach cancer, pancreatic cancer, and colorectal cancer surgeries, especially in hepatic resection requiring hemostasis. The hemostatic agent may be used also as embolus material to coagulate blood in a cerebral aneurysm or a varicose vein or used in embolization therapy for cancer. In the hemostasis method, the second agent is dissolved in an aqueous solvent preferably immediately prior to the use as mentioned above. A concentration of the crosslinking agent in the aqueous solution is as described above. Then, thus obtained aqueous solution of the second agent may be placed in a vacant syringe of the dual syringe dispenser, of which other syringe is filled with an aqueous solution of the first agent, and the first and the second agent are applied or sprayed by an air-assisted spray to an affected site of a subject.

The present invention will be explained with reference to the following Examples, but the present invention is not limited thereto.

EXAMPLES

Examples 1-40

Preparation of the First Agent

The gelatin derivatives 1-10 as shown in Table 1 were prepared. The specific method of the preparation is explained for gelatin derivative 2 as an example. In Table 1, the number of carbon atoms shown in the column designated as "Hydrophobic group" is a total carbon number in the moiety, $CHR^1R^2$, in the aforesaid formula (1). Alaska pollock-derived gelatin (Mw 20,000, Nitta Gelatin Inc.) was dissolved in 350 mL of water and then, to the aqueous solution thus obtained, 140 mL of ethanol was added and stirred at 50° C. Separately, decanal in an amount of about 1.5 equivalents of a stoichiometric amount corresponding to a derivatization ratio of 10 mol % was dissolved in 5 mL of ethanol and was mixed with the gelatin solution. Subsequently, 2-picoline borane in an amount of about 1.5 equivalents of decanal was added and stirred for 18 hours. The produced gelatin derivative was precipitated by adding dropwise cold ethanol in an amount of 10 times the volume of the reaction mixture, and then was suction filtered. The obtained filtration residue was placed in cold ethanol in an amount of about 5 times the volume of the residue and washed while stirring for one hour, followed by suction filtration. After repeating this washing process for three times, the product was vacuum dried for 2 days and a white gelatin derivative having decyl group was obtained with about 84% yield. The derivatization ratio was determined colorimetrically by a titration method using trinitrobenzenesulfonic acid.

The other gelatin derivatives were prepared in the same manner as described above except that the molecular weight (Mw) of Alaska pollock-derived gelatin and derivatization ratio were varied, and that octanal or undecanal was used in place of decanal.

TABLE 1

| Gelatin derivative | | Gelatin | Derivatization ratio | Hydrophobic |
|---|---|---|---|---|
| No. | Name | (Mw) | (mol %) | group |
| 1 | 8.3C8 | 20,000 | 8.3 | C8 |
| 2 | 9.5C10 | 20,000 | 9.5 | C10 |
| 3 | 12.0C10 | 20,000 | 12.0 | C10 |
| 4 | 9.5C12 | 20,000 | 9.5 | C12 |
| 5 | 15.0C12 | 20,000 | 15.0 | C12 |
| 6 | 5.8C8 | 35,000 | 5.8 | C8 |
| 7 | 6.5C10 | 35,000 | 6.5 | C10 |
| 8 | 9.3C10 | 35,000 | 9.3 | C10 |
| 9 | 6.9C12 | 35,000 | 6.9 | C12 |
| 10 | 8.9C12 | 35,000 | 8.9 | C12 |

Each of the above gelatin derivatives obtained was dissolved in 0.1M borate buffer having a pH of 9.0 or 9.5 at a concentration of 15 w/v %. The solution thus obtained was placed in a 2 mL-polypropylene disposable double syringe and thereby each first agent was obtained.

Preparation of the Second Agent

As a second agent, pentaerythritol poly(ethylene)glycol ether tetrasuccinimidyl glutarate (4S-PEG, Mw=20,000 or 10,000, Sigma-Aldrich, Co. LLC) was used. Just before conducting each characterization described below, 4S-PEG was dissolved in a phosphate buffer having a pH of 4 and comprising 100 pig/mL of brilliant blue. An amount of 4S-PEG was such that a molar equivalent ratio of the succinimidyl ester group thereof to the remaining amino groups in the first agent was 0.5 when the same volume of first agent and the second agent solutions were used. The aqueous solution of the second agent thus obtained was placed in the vacant syringe of the dual syringe dispenser containing the first agent solution, and thereby second agents of Examples 1-40 shown in Table 2 were obtained.

TABLE 2

| Example | First agent | | Second agent |
|---|---|---|---|
| No. | Gelatin derivative | pH | Mw |
| 1 | 8.3C8 | 9.0 | 20,000 |
| 2 | 9.5C10 | 9.0 | 20,000 |

TABLE 2-continued

| Example | First agent | | Second agent |
|---|---|---|---|
| No. | Gelatin derivative | pH | Mw |
| 3 | 12.0C10 | 9.0 | 20,000 |
| 4 | 9.5C12 | 9.0 | 20,000 |
| 5 | 15.0C12 | 9.0 | 20,000 |
| 6 | 5.8C8 | 9.0 | 20,000 |
| 7 | 6.5C10 | 9.0 | 20,000 |
| 8 | 9.3C10 | 9.0 | 20,000 |
| 9 | 6.9C12 | 9.0 | 20,000 |
| 10 | 8.9C12 | 9.0 | 20,000 |
| 11 | 8.3C8 | 9.5 | 20,000 |
| 12 | 9.5C10 | 9.5 | 20,000 |
| 13 | 12.0C10 | 9.5 | 20,000 |
| 14 | 9.5C12 | 9.5 | 20,000 |
| 15 | 15.0C12 | 9.5 | 20,000 |
| 16 | 5.8C8 | 9.5 | 20,000 |
| 17 | 6.5C10 | 9.5 | 20,000 |
| 18 | 9.3C10 | 9.5 | 20,000 |
| 19 | 6.9C12 | 9.5 | 20,000 |
| 20 | 8.9C12 | 9.5 | 20,000 |
| 21 | 8.3C8 | 9.0 | 10,000 |
| 22 | 9.5C10 | 9.0 | 10,000 |
| 23 | 12.0C10 | 9.0 | 10,000 |
| 24 | 9.5C12 | 9.0 | 10,000 |
| 25 | 15.0C12 | 9.0 | 10,000 |
| 26 | 5.8C8 | 9.0 | 10,000 |
| 27 | 6.5C10 | 9.0 | 10,000 |
| 28 | 9.3C10 | 9.0 | 10,000 |
| 29 | 6.9C12 | 9.0 | 10,000 |
| 30 | 8.9C12 | 9.0 | 10,000 |
| 31 | 8.3C8 | 9.5 | 10,000 |
| 32 | 9.5C10 | 9.5 | 10,000 |
| 33 | 12.0C10 | 9.5 | 10,000 |
| 34 | 9.5C12 | 9.5 | 10,000 |
| 35 | 15.0C12 | 9.5 | 10,000 |
| 36 | 5.8C8 | 9.5 | 10,000 |
| 37 | 6.5C10 | 9.5 | 10,000 |
| 38 | 9.3C10 | 9.5 | 10,000 |
| 39 | 6.9C12 | 9.5 | 10,000 |
| 40 | 8.9C12 | 9.5 | 10,000 |

Comparative Examples 1-8

Comparative hemostatic agents as shown in Table 3 were prepared in the same manner as the above Examples except that non-derivatized gelatins (Mw=20,000 or 35,000) were used as the first agents. In Table 3, "Comp.Ex." stands for "Comparative Example."

TABLE 3

| Comp. Ex. | First agent | | Second agent |
|---|---|---|---|
| No. | Mw | pH | Mw |
| 1 | 20,000 | 9.0 | 20,000 |
| 2 | 35,000 | 9.0 | 20,000 |
| 3 | 20,000 | 9.5 | 20,000 |
| 4 | 35,000 | 9.5 | 20,000 |
| 5 | 20,000 | 9.0 | 10,000 |
| 6 | 35,000 | 9.0 | 10,000 |
| 7 | 20,000 | 9.5 | 10,000 |
| 8 | 35,000 | 9.5 | 10,000 |

Characterization

1. In Vitro Blood Coagulation Rate

In a 5 mL glass vial, blood (porcine whole blood comprising 0.324 w/v % (12.6 mM) of sodium citrate for transfusion) was placed, to which the hemostatic agent of Example 2 was added and immediately a 1.5 mm-long stirring bar coated with polytetrafluoroethylene was also added. Then, the vial was placed on a hot plate heated at 37° C. and the contents in the vial was stirred at 280 rpm. A time for the stirring bar to stop rotating due to the blood coagulation was measured. A total volume of the blood and the hemostatic agent was fixed to 1 mL with a volume of the blood being varied from 250 µL (i.e., 0.75 volume ratio of the hemostatic agent), 500 µL (i.e., 0.5 volume ratio of the hemostatic agent), to 750 µL (i.e., 0.25 volume ratio of the hemostatic agent) and the measurements, for each volume ratio, were repeated for three times of which average was determined. The Comparative Example 1 was subjected to the same measurement. The results are shown in Table 4 and in FIG. 2.

2. In Vitro Blood Coagulation Rate in the Presence of Ca Ion

The same measurements as in Characterization 1 above were performed except that, prior to the addition of the hemostatic agent, a 251.9 mM calcium chloride aqueous solution was added to the porcine whole blood in a volume ratio relative to the porcine whole blood of 1/20 (i.e., 0.048 wt % Ca ion in the porcine whole blood). The same measurement was performed on Comparative Example 1. The results are shown in Table 4 and FIG. 2. In Table 4, "SD" stands for standard deviation.

TABLE 4

| | | Vol. ratio of hemostatic agent | Coagulation time(s) | | | | |
|---|---|---|---|---|---|---|---|
| | | | 1 | 2 | 3 | Avg. | SD |
| Blood coagulation rate | Comp. Ex. 1 | 0.75 | 4.59 | 2.93 | 5.08 | 4.20 | 1.12 |
| | | 0.50 | 11.84 | 19.02 | 10.01 | 13.62 | 4.76 |
| | | 0.25 | 56.50 | 58.72 | 50.23 | 55.15 | 4.40 |
| | Example 2 | 0.75 | 4.25 | 3.67 | 2.33 | 3.41 | 0.98 |
| | | 0.50 | 7.88 | 7.02 | 4.16 | 6.35 | 1.95 |
| | | 0.25 | 33.10 | 21.89 | 32.79 | 29.26 | 6.39 |
| Blood coagulation rate (+Ca ion) | Comp. Ex. 1 | 0.75 | 3.05 | 2.65 | 2.01 | 2.57 | 0.52 |
| | | 0.50 | 16.57 | 6.97 | 6.50 | 10.01 | 5.68 |
| | | 0.25 | 22.50 | 35.43 | 31.55 | 29.83 | 6.63 |
| | Example 2 | 0.75 | 2.03 | 2.98 | 4.62 | 3.21 | 1.31 |
| | | 0.50 | 4.35 | 7.80 | 9.04 | 7.06 | 2.43 |
| | | 0.25 | 26.25 | 33.61 | 25.21 | 28.36 | 4.58 |

Figure 2:
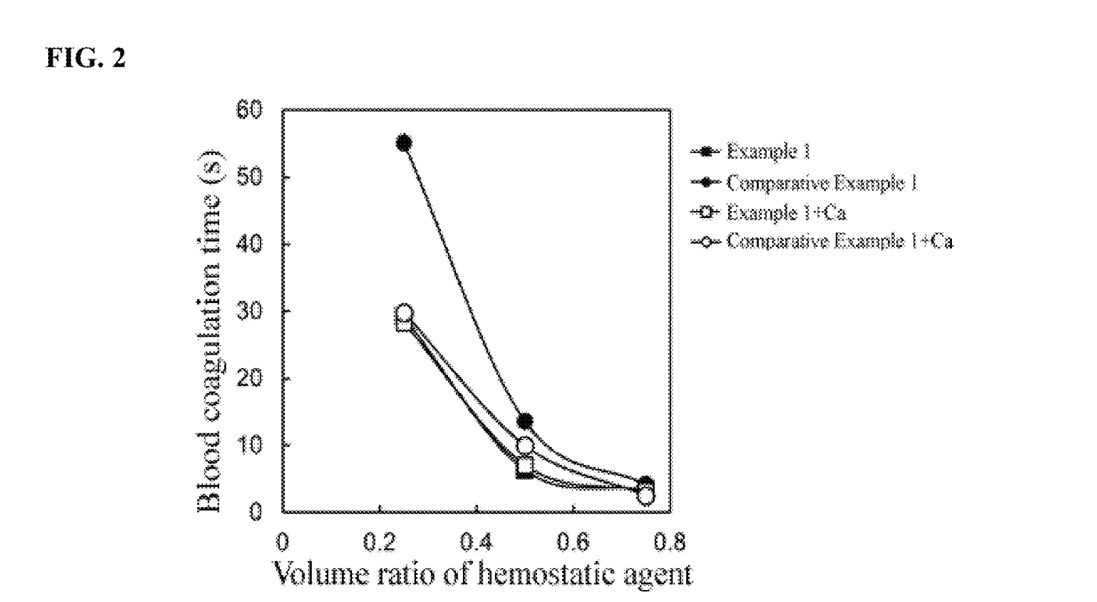
FIG. 2 shows a graph comparing in vitro blood coagulation time of Example 2 with that of Comparative Example 1.

FIG. 2 shows the graph comparing in vitro blood coagulation time of Example 2 with that of Comparative Example 1. At the increased ratio of the hemostatic agent (i.e., 0.75 volume ratio of the hemostatic agent), almost identical coagulation time was observed regardless of the presence of hydrophobic group or Ca ion. In the absence of Ca ion, the hemostatic agent of Comparative Example 1 showed significantly longer coagulation time with decreased amount of the hemostatic agent. On the other hand, the hemostatic agent of Example 2 showed shorter coagulation time independent of the presence of Ca ion. This means that the hydrophobically modified gelatin achieves sufficient hemostatic effect even without adding Ca ion, which is inevitable for fibrin-based hemostatic agent.

3. In Vitro Blood Coagulation Rate at 0.5 Volume Ratio of the Hemostatic Agent

Figure 3A:
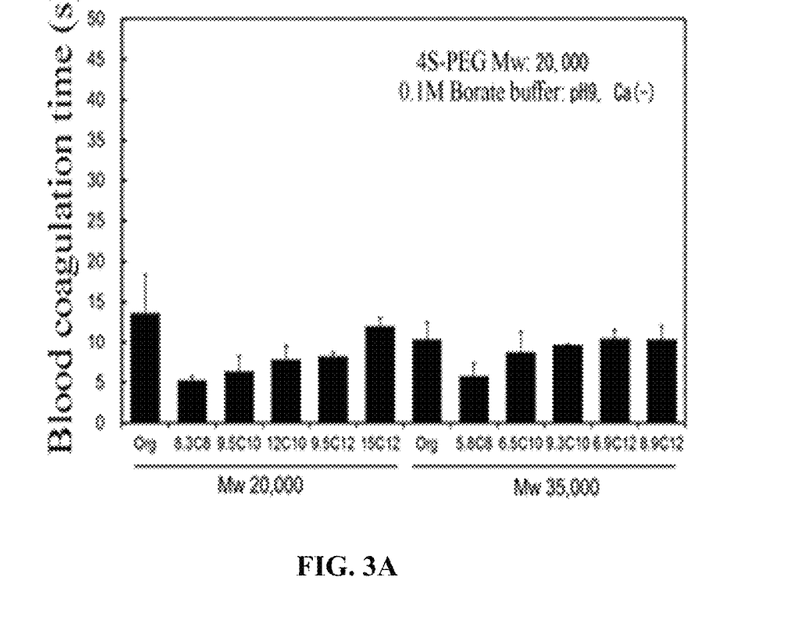
FIG. 3A shows a graph comparing in vitro blood coagulation time of Examples 1 to 5 with that of Comparative Example 1 and comparing Example 6-10 with that of Comparative Example 2.
Figure 3B:
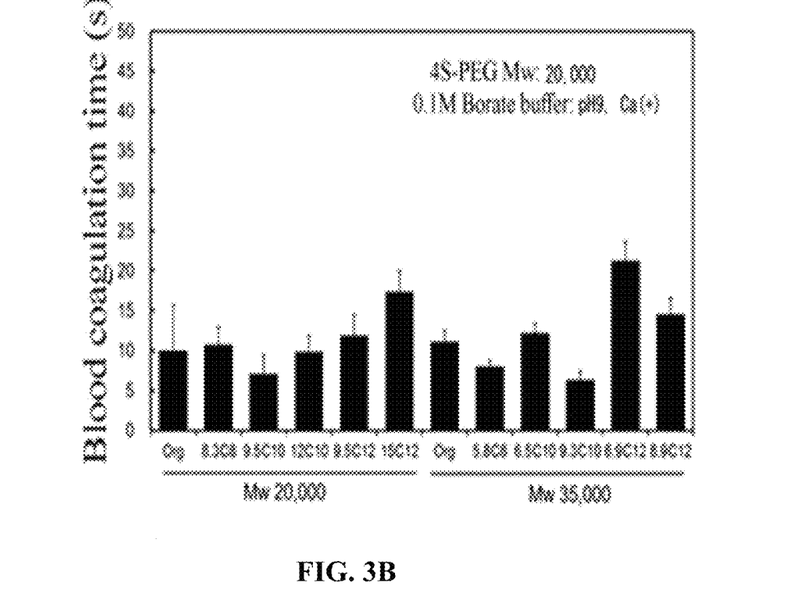
FIG. 3B shows a graph comparing in vitro blood coagulation time as in FIG. 3A in the presence of Ca ion.
Figure 4A:
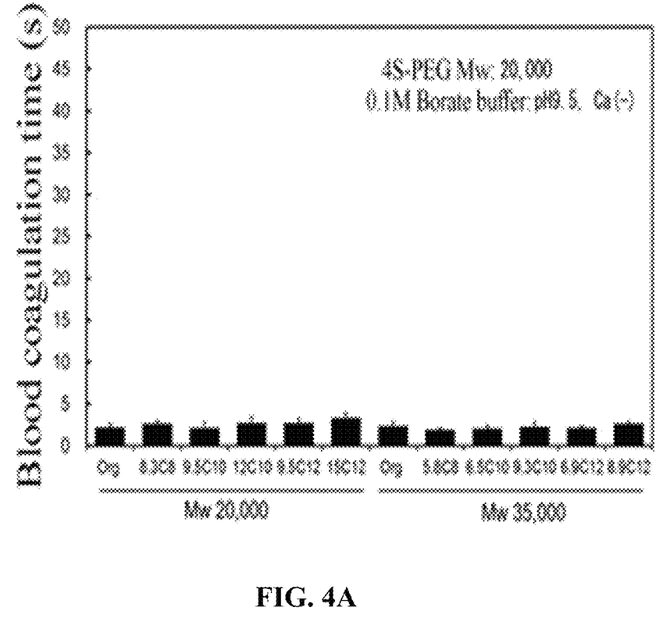
FIG. 4A shows a graph comparing in vitro blood coagulation time of Examples 11 to 15 with that of Comparative Example 3 and comparing Example 16-20 with that of Comparative Example 4.
Figure 4B:
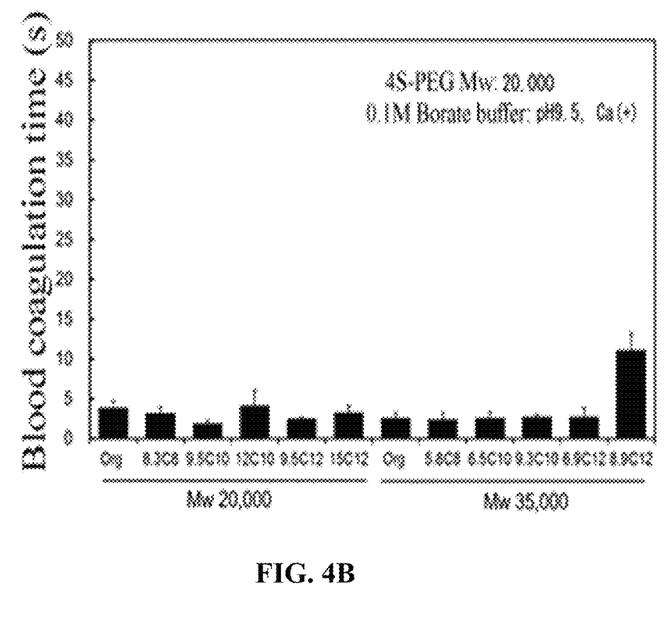
FIG. 4B shows a graph comparing in vitro blood coagulation time as in FIG. 4A in the presence of Ca ion.
Figure 5A:
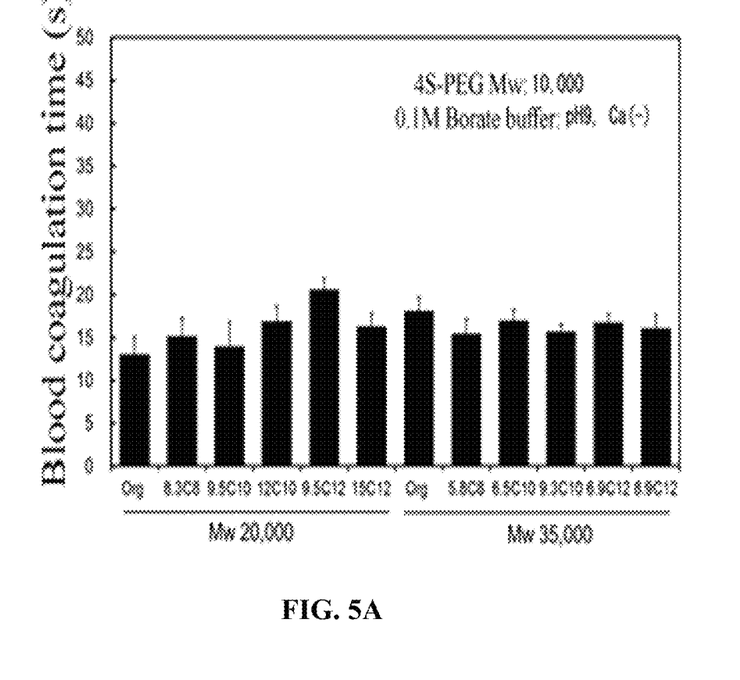
FIG. 5A shows a graph comparing in vitro blood coagulation time of Examples 21 to 25 with that of Comparative Example 5 and comparing Example 26-30 with that of Comparative Example 6.
Figure 5B:
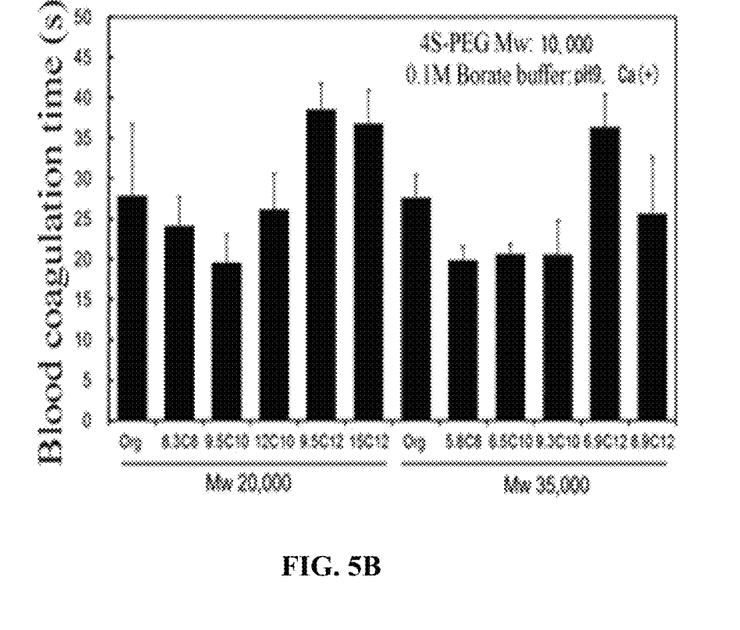
FIG. 5B shows a graph comparing in vitro blood coagulation time as in FIG. 5A in the presence of Ca ion.
Figure 6A:
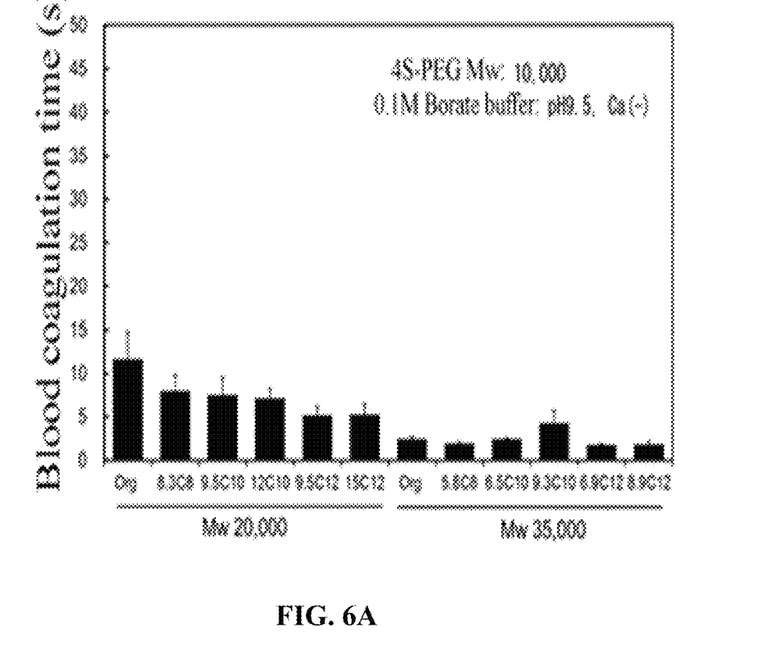
FIG. 6A shows a graph comparing in vitro blood coagulation time of Examples 31 to 35 with that of Comparative Example 7 and comparing Example 26-30 with that of Comparative Example 8.
Figure 6B:
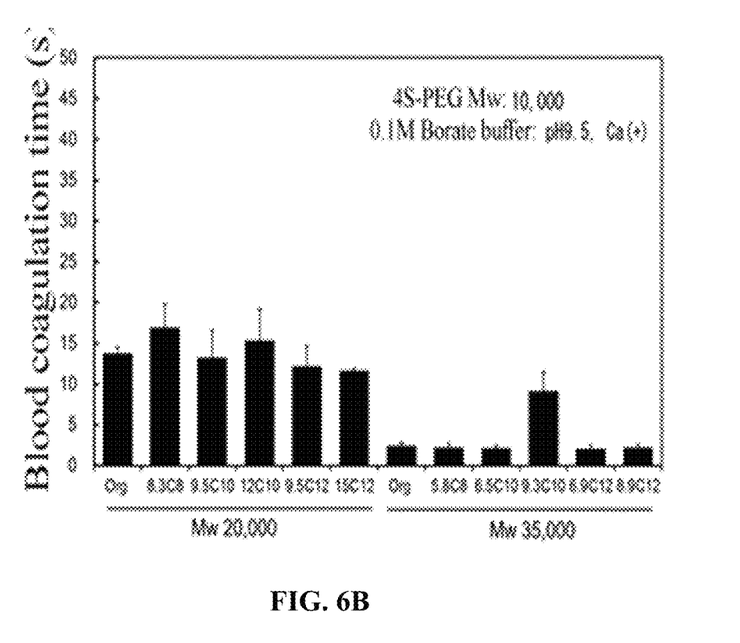
FIG. 6B shows a graph comparing in vitro blood coagulation time as in FIG. 6A in the presence of Ca ion.

The time for blood coagulation of the hemostatic agents of Examples 1, 3-40 was measured in the same manner as described for the Characterization 1 and 2 above to study influences on blood coagulation rate of the carbon number of the hydrophobic group, the derivatization ratio, the molecular weight of the gelatin, pH of the borate buffer, the molecular weight of the crosslinking agent and the presence of Ca ion. The results are shown in FIG. 3A to 6b obtained when the volume ratio of the hemostatic agent was fixed to 0.5. In each figure, "Org" represents Comparative Example, which is different from Examples shown in the same figure only in that the gelatin was not derivatized. For example, in FIG. 3A, "Org" at the left end represents Comparative Example 1 and that in the center represents Comparative Example 2. In FIG. 3A and so on, "Ca(−)" indicates the absence of Ca ion, while "Ca(+)" indicates the presence of Ca ion.

As shown in FIGS. 3A to 6B, most of the hemostatic agents of Examples showed faster blood coagulation than the corresponding Comparative Examples which were different from Examples only in that the gelatin was not derivatized. Some hemostatic agents having a hydrophobic group with a larger number of carbon atoms showed slower blood coagulation than the corresponding Comparative Example, but it is considered that they show faster blood coagulation in vivo because of the higher affinity to the epithelial tissue of the hydrophobic groups. In fact, the hemostatic agent of Example 8, for instance, demonstrated significantly smaller amount of hemorrhage than Comparative Example 2 in vivo as shown in Table 5, although it showed about the same coagulation rate as Comparative Example 2 in FIG. 3A. Among various factors, pH of the first agent and a molecular weight of the second agent have relatively large effects on the blood coagulation time. For example, when the first agent had a pH of 9.5 (FIG. 4A), all of the examples showed faster blood coagulation than the examples where the first agent had a pH of 9.0 (FIG. 3A). Faster blood coagulation was observed for the examples comprising the second agent with a molecular weight of 20,000 (FIG. 3A) than those with 10,000 (FIG. 5A). This suggest that a blood coagulation rate can be controlled by adjusting these factors. In the presence of Ca ion, blood coagulation rate tended to be slower particularly when the second agent had a smaller molecular weight, of which reason is unknown.

4. Amount of In Vivo Hemorrhage

The hemostatic agents of Example 8 and Comparative Example 2 were compared by the following procedures according to the evaluation method proposed by Murakami et al. (Colloids and Surfaces B: Biointerfaces 65 (2008) 186-189).

(1) A 7-week-old rat (Wister rat, an average weight of about 300 g) intraperitoneally anesthetized with sodium pentobarbital (SOMUNOPENTYL, trade name, Sumitomo Dainippon Pharma Co., Ltd.) was fixed on a medical cork board and incised in the abdomen.

(2) After carefully removing the serous fluid, a pre-weighted filter paper was placed beneath the liver, beneath which a Parafilm (trade name) was placed to prevent the filter paper from absorbing gradually oozing serous fluid.

(3) The cork board was tilted and kept at an angle of 45° relative to a horizontal plane to assist the flow of the bleeding from the liver to the filter paper.

(4) The liver was pricked with a sterilized needle (18 G, 38 mm, Terumo Co.) and immediately the hemostatic agent was applied to the liver wound. After standing 3 minutes, the filter paper was weighed (w1, mg).

(5) As a blank, the hemostatic agent was applied without having pricked the liver and the filter paper was weighed (w3, mg) after standing 3 minutes.

(6) An amount of hemorrhage (w1-w3) (mg) was calculated. The results are shown in Table 5.

An amount of hemorrhage without using a hemostatic agent was not measured because the purpose of this test was not to evaluate hemostatic efficacy relative to the natural hemostasis but to compare hemostatic agents.

TABLE 5

| | w1 (mg) | w3 (mg) | Amount of hemorrhage (w1 − w3) (mg) | (w1 − w3)/w3 | Amount of hemorrhage per weight (mg/g) |
|---|---|---|---|---|---|
| Example 8 | 458.6 | 340.7 | 117.9 | 0.4 | 0.4 |
| Comp. Ex. 2 | 586.0 | 368.2 | 217.8 | 0.6 | 0.7 |
| Literature | 180.8 | 137.0 | 43.8 | 0.3 | 1.8 |

In Table 5, "Literature" represents the data described in Murakami et al. (page 188, the right column) of a fibrin-based hemostatic agent (TISSEEL, trade name, Baxter Ltd.). As can be found from the table, the hemostatic agent of Example 8 showed significantly smaller amount of hemorrhage, i.e., (w1-w3), than the hemostatic agent composed of the non-derivatized gelatin (Comparative Example 2), indicating a superior hemostasis efficacy of the hemostasis using the hemostatic agent of Example 8. The amount of hemorrhage, (w1-w3), of Example 8 was about 3 times larger than that of the literature. However, considering that the rat with an average weight of about 300 g was used in this test while the mouse with an average weight of 24.3 g was used in the literature and that a volume of applied hemostatic agent was larger than that used in the literature as shown in about 2.5 times larger value of W3 (340.7 mg) than that in the literature (137.0 mg), Example 8 shows roughly comparable value to the literature in an amount of hemorrhage per applied hemostatic agent, i.e., (w1-w3)/w3, and significantly smaller value in an amount of hemorrhage per body weight, 0.39 mg/g, than the literature, 1.80 mg/g.

INDUSTRIAL APPLICABILITY

The method of hemostasis of the present invention is very useful in various surgical operations such as those in thoracic surgery, gastrointestinal surgery, cardiovascular surgery, orthopedic surgery, oral and maxillofacial surgery, and cancer surgery.

What is claimed is:

1. A method of hemostasis, comprising the step of:
   applying a hemostatic agent to an affected site of a subject in need thereof, wherein the hemostatic agent consisting of
   a first agent comprising a gelatin derivative that comprises a hydrophobic group bonded to a gelatin via an imino group, wherein the gelatin derivative has
   (a) a weight average molecular weight of from 10,000 to 50,000,
   (b) the hydrophobic group, which is an alkyl group having 6 to 18 carbon atoms; and
   (c) a molar ratio of imino group/amino group of the gelatin derivative ranging from 1/99 to 30/70; and
   a second agent comprising a crosslinking agent for the gelatin derivative.

2. The method of hemostasis according to claim 1, wherein the first agent is applied in the form of an aqueous solution having a pH of from 8 to 11, and the second agent is applied in the form of an aqueous solution having a pH of from 3 to 8.

3. The method of hemostasis according to claim 2, wherein the first agent and the second agent are applied by using a dual syringe dispenser.

4. The method of hemostasis according to claim 1, wherein the gelatin is Alaska pollock-derived gelatin.

5. The method of hemostasis according to claim 1, wherein the crosslinking agent is pentaerythritol polyethylene glycol ether tetrasuccinimidyl glutarate having a weight average molecular weight of from 3,000 to 30,000.

6. The method of hemostasis according to claim 1, wherein the first agent and the second agent are applied in such an amount that a ratio of an equivalent amount of functional group of the crosslinking agent to an equivalent amount of amino group in the gelatin derivative ranges from 0.1 to 3.

* * * * *